(12) United States Patent
Siegele et al.

(10) Patent No.: US 10,092,447 B2
(45) Date of Patent: Oct. 9, 2018

(54) INTRODUCING BUBBLES TO IMPROVE CORNEA RESHAPING WITHOUT THE CREATION OF A FLAP

(71) Applicants: Nicholas S. Siegele, Austin, TX (US); The Trustees of Princeton University, Princeton, NJ (US)

(72) Inventors: Nicholas S. Siegele, Austin, TX (US); Li Deng, Princeton, NJ (US); Szymon Suckewer, Princeton, NJ (US)

(73) Assignees: Nicholas S. Siegele, Austin, TX (US); Deng Li, Princeton, NJ (US); Szymon Suckewer, Princeton, NJ (US)

( * ) Notice: Subject to any disclaimer, the term of this patent is extended or adjusted under 35 U.S.C. 154(b) by 207 days.

(21) Appl. No.: 15/138,944

(22) Filed: Apr. 26, 2016

(65) Prior Publication Data

US 2016/0262934 A1 Sep. 15, 2016

Related U.S. Application Data

(62) Division of application No. 13/719,605, filed on Dec. 19, 2012, now Pat. No. 9,339,335.

(51) Int. Cl.
*A61B 18/20* (2006.01)
*A61F 9/008* (2006.01)
*A61F 9/013* (2006.01)

(52) U.S. Cl.
CPC .......... *A61F 9/00827* (2013.01); *A61B 18/20* (2013.01); *A61F 2009/0088* (2013.01); *A61F 2009/00872* (2013.01); *A61F 2009/00897* (2013.01)

(58) Field of Classification Search
CPC ................................ A61B 18/20; A61F 9/013
See application file for complete search history.

(56) References Cited

U.S. PATENT DOCUMENTS

| 2008/0051772 A1* | 2/2008 | Suckewer | ........... A61F 9/00827 606/5 |
| 2012/0046680 A1* | 2/2012 | Dishler | ............... A61F 9/00827 606/166 |

* cited by examiner

*Primary Examiner* — William Levicky
(74) *Attorney, Agent, or Firm* — Sprinkle IP Law Group

(57) ABSTRACT

Ultra-short pulsed laser radiation is applied to a patient's eye to create a row of bubbles oriented perpendicular to the axis of vision. The row of bubbles leads to a region of the eye to be ablated. In a second step, a femtosecond laser beam guided through the row of bubbles converts it to a channel perpendicular to the axis of vision. In a third step, a femtosecond laser beam is guided through the channel to ablate a portion of the eye. Using a femtosecond laser with intensity in the range of $10^{11}$-$10^{15}$ W/cm$^2$ for the second and third steps facilitates multi-photon ablation that is practically devoid of eye tissue heating. Creating bubbles in the first step increases the speed of channel creation and channel diameter uniformity, thereby increasing the precision of the subsequent multi-photon ablation.

16 Claims, 4 Drawing Sheets

INTRODUCING BUBBLES TO IMPROVE CORNEA RESHAPING WITHOUT THE CREATION OF A FLAP

CROSS-REFERENCE TO RELATED APPLICATIONS

This application is a continuation of U.S. patent application Ser. No. 13/719,605, filed Dec. 19, 2012, by Nicholas S. Siegele, et al., which is incorporated by reference as if set forth herein in its entirety.

BACKGROUND

1. Field of the Invention

This invention relates to methods of, and apparatus for eye surgery, and more particularly to a laser method and apparatus for corneal and intraocular surgery, as well as vision correction.

2. Description of the Related Art

With the development of laser procedures such as LASIK to help correct eye-sight or vision, by reshaping the cornea of the eye, several other new laser eye-procedures are being considered that concern the photo-ablation of eye tissue.

U.S. Pat. No. 4,538,608, issued to L'Esperance, Jr. for "Method and Apparatus for Removing Cataractous Lens Tissue by Laser Radiation" teaches how to deliver laser energy into the anterior of the eye lens and scan the laser beam in order to photo-ablate cataractous tissue, and has general importance for the process of photo-ablation of eye tissue, including photo-ablation of stroma. This procedure was improved by J. Bille (U.S. Pat. No. 5,246,435 "Method for Removing Cataractous Material"), who invented a procedure of laser energy delivery to separate lamellae in the stroma by focusing a laser beam between lamellae layers and photo-ablating tissue at the interface between these layers.

In those inventions, nanosecond (nsec) type laser beams were considered (for example, 10-20 nsec excimer lasers, or 5-10 nsec Nd/YAG lasers; 1 nsec=$1\times10^{-9}$ sec). With these pulse durations, each laser shot, in addition to ablating tissue, creates strong shock waves within the eye and generates significant tissue heating. These effects are undesirable, and may be reduced by using lasers with shorter pulse durations. Therefore, when compact ultra-short lasers, those with pulse durations less than 1 picosecond (1 psec), [1 psec=$10^{-12}$ sec], were developed in the late 1980's, they were considered for use in eye surgery.

In the review article by Christopher Yo et al. on "LASIK, Future Advances" (E-Medicine, Nov. 25, 2004) the authors stressed (page 5) that " . . . one can assume the culprit that negates all the advantages of custom ablation may lie in the flap procedure itself. Hence, it would be a great leap in refractive surgery if the LASIK procedure can one day be completed intrastromally without the need for cutting a flap." In addition, the LASIK flap may lead to complications such as flap striae, epithelial ingrowths beneath the flap, diffuse lamellar keratitis, and flap tears. The present invention responds exactly to the desirable outcome of corneal refractive surgery without a flap, namely reshaping the cornea by means of using high intensity femtosecond (fsec) laser pulses for correcting the refractive errors of myopia, hyperopia, and astigmatism without cutting a flap (1 femtosecond=1 fsec=$1\times10^{-15}$ sec).

The general advantage of using fsec lasers for eye surgery compared to using much longer pulse lasers (nsec-type excimer, Nd/YAG or Nd/Glass lasers) is that with fsec lasers there is a much lower energy requirement, in particular when the surgery requires eye tissue ablation, that is, photo-ablation. Photo-ablation is a thermal process that requires a certain intensity of laser beam, typically in the range of $10^9$-$10^{11}$ W/cm$^2$. For the same ablated spot size, the intensity required for photo-ablation is inversely proportional to the pulse duration. For example, laser pulses of 100 fsec duration can provide photo-ablation at hundreds of times smaller beam energies than when laser pulses of 10 nsec duration are used. Being able to use smaller beam energies, ultra-short laser pulses can provide tissue cuts with less eye trauma, as was proven experimentally. This observation leads to three principal advantages of using ultra-short laser pulses for eye surgery. One advantage is that it is possible to perform much higher precision tissue cuts with such lasers when compared with nanosecond-type lasers. A second advantage is that ultra-short laser pulses produce much smaller heating effects in tissue when compared with longer laser pulses, greatly reducing tissue damage. A third advantage is that ultra-short laser pulses produce only very weak shock waves in tissue, whereas long laser pulses produce very substantial shock waves resulting in considerable trauma. In eye surgery, this trauma can have substantial negative effects on the prognosis following surgery, such as inflammation and undesirable wound healing.

In addition to photo-ablation, laser pulses can be used to produce photo-disruption, which is also a thermal process. The photo-disruption process can result in the formation of bubbles, i.e. cavity bubbles or gas bubbles in the tissue. This requires significantly less intensity than photo-ablation, typically in the range of $10^8$-$10^9$ W/cm$^2$.

In conventional LASIK procedures, where a flap is created by using a mechanical microkeratome, photo-disruption provides the basis for replacing the mechanical flap cut with a much more precise flap cut using a fsec laser [Juhasz et al., U.S. Pat. No. 5,993,438 (issued Nov. 30, 1999) "Intrastromal photorefractive keratectomy", T. Juhasz, U.S. Pat. No. 6,110,116 (issued Aug. 29, 2000) "Method for corneal laser surgery", and T. Juhasz et al., U.S. Pat. No. 6,146,375 (issued Nov. 14, 2000) "Device and method for internal surface sclerostomy"]. U.S. Pat. No. 6,146,375 also teaches about using fsec or picosecond (psec) pulses for the treatment of glaucoma. T. Juhasz et al.'s research has led to the successful company "IntraLase" that markets the procedure for cutting the flap with a fsec laser in preparation for LASIK eye surgery, where the corneal correction itself uses an excimer laser providing pulses of 10-20 nsec duration.

In The patent application "Method and Device for Corneal Reshaping by Intrastromal Tissue Removal" by S. Suckewer, P. Hersh, A. Smits, and A. Morozov, published by US Patent Office on Feb. 28, 2008 (Pub. No: US 2008/0051772 A1) a new approach to cornea reshaping is described. This invention teaches how to apply a laser beam to reshape the eye's cornea under the cornea's surface without creating or removing a flap, hence it is called Flapless LASIK.

Flapless LASIK is a two-step procedure. The first step creates long and narrow channels in the cornea with a laser beam oriented approximately perpendicular to the axis of vision. Such channels lead to the regions that are to be ablated. In the second step, the fsec laser beam, through such channels, reaches the stroma between the inner (endothelial) and outer (superficial) cornea and results in ablation of the stroma at a spot. By changing the position of the focusing lens or focusing mirror, the location of the ablation spot moves along the channel. Controlling the number of laser pulses for each spot controls the amount of ablated material in each spot. The preferred laser beams consist of ultra-short pulses of duration 30-200 fsec, although the duration could be shorter or longer, at repetition rates of 1,000-10,000 Hz, with higher or lower repetition rates possible as well, and intensity in the range of $10^{13}$-$10^{15}$ watts/cm$^2$, resulting in what the inventors termed "multi-photon ablation".

SUMMARY OF THE INVENTION

The present invention relates to improving the Flapless LASIK method by adding an additional initial step prior to creating the channel by creating bubbles by photo-disruption under the surface of the cornea in order to increase the speed of the laser beam penetrating into the area of corneal ablation. In a preferred embodiment, this improved Flapless LASIK may be is a three-step procedure. The additional first step uses preferably an fsec laser beam that is typically oriented parallel to the axis of vision to create, via photo-disruption, one or more long and narrow rows of bubbles in the cornea that are oriented approximately perpendicular, or at a greater or lesser angle, to the axis of vision. Such bubble rows lead to the regions that are to be ablated.

In the next step, the fsec laser beam of much higher intensity than the laser beam applied for the first step, through such bubble rows, reaches the stroma between the inner (endothelial) and outer (superficial) cornea, creating a channel using multi-photon ablation. In the next step, the fsec beam, after reaching the stroma, ablates the stroma at a spot using multi-photon ablation. By changing the position of the focusing lens or focusing minor, the location of the ablation spot can moves along the channel. Because it may be is preferable to use minimum pulse energy, hence minimum pulse intensity, to create the channel by multi-photon ablation in order to keep the channel at a relatively small diameter, it may be desirable to increase the laser pulse energy and its intensity in this said third step. This can easily be accomplished by changing the voltage on the power supply to the laser amplifier or by increasing the diaphragm that limits the laser beam's diameter. Moreover, controlling the number of laser pulses for each spot is a method to controls the amount of ablated material in each spot.

The bubbles created in the first step may not only increase the speed of the ablation channel's creation in the cornea, thus increasing the rate of ablation, but also may make the diameter of such channels more uniform, hence decreasing energy losses of high intensity fsec laser pulses during their propagation through the channels and improving the precision of the stromal ablation.

In the present invention the fsec laser beam is divided into 2 beams, although a single beam at any given time or two or more separate laser beam sources could be used. The first beam, which may be of very low pulse energy in the a range of 1 to 10 micro-Joule (μJ), which could be higher or lower, and intensity in the range $10^8$ to $10^9$ W/cm$^2$, which could be higher or lower, can be is delivered to the eye approximately along the vision axis, hence approximately perpendicular to the second laser beam, to create at least one line of bubbles that run approximately perpendicular to the axis of sight. The second beam then creates a channel through the bubble row or rows by means of multi-photon ablation, and after reaching the end of the channel or the ablation target, ablates the chosen areas also using multi-photon ablation.

The first beam creates bubbles at depths of 150-250 μm below the surface of the cornea, although it could be shallower or deeper, along an approximately straight line as a precursor for the channel. The bubbles are created using photo-disruption and their creation does not damage the cornea. Bubbles are typically created in one to two rows, but there can be more rows, next to each other on a plane approximately parallel to the surface of the cornea. In addition to this method for creating the bubble row(s), a cylindrical lens can be implemented with the femtosecond laser oriented approximately parallel to the axis of vision, which creates one row of bubbles per pulse from the fsec laser. Thus one or more rows of bubbles can be created, stretching from the edge of the eye's cornea to the point of ablation in the stroma, in a very short period of time, whereas the main ablation beam then passes through between approximately tens of nanoseconds and tens of microseconds later.

The present invention, improved Flapless LASIK, has been demonstrated on fresh pig eyes from an eye bank. Using a 50 fsec or 100 fsec, approximately from 1 to 10 μJ laser beam, which was tightly focused with a short focal length lens down to a range of 30 to 100 μm diameter on a plane approximately parallel to the cornea's surface, one, two or even three rows of bubbles were created. The focused fsec or psec laser beam spot moved along the stroma, at a speed of approximately 0.25 mm/s or faster, to form a bubble region. Introducing the laser ablation beam into the row(s) of bubbles, the speed of creation of a 3 mm channel from the edge of the cornea to the area required for ablation was 1.5-2 times faster than without bubbles, all other conditions being the same in both cases. This idea, of course, can be applied to two or more laser ablating beams.

The importance of this invention is three-fold, namely it improves the uniformity of the channels leading to lower losses of energy of laser beams during their propagation through the channels, decreases the time of the stroma ablation procedure, and improves the precision of said stroma ablation.

Various implements are known in the art, but fail to address all of the problems solved by the invention described herein. Various embodiments of this invention are illustrated in the accompanying drawings and will be described in more detail herein below.

BRIEF DESCRIPTION OF THE DRAWINGS

Other objects and advantages of the invention may become apparent upon reading the following detailed description and upon reference to the accompanying drawings.

Figure 1:
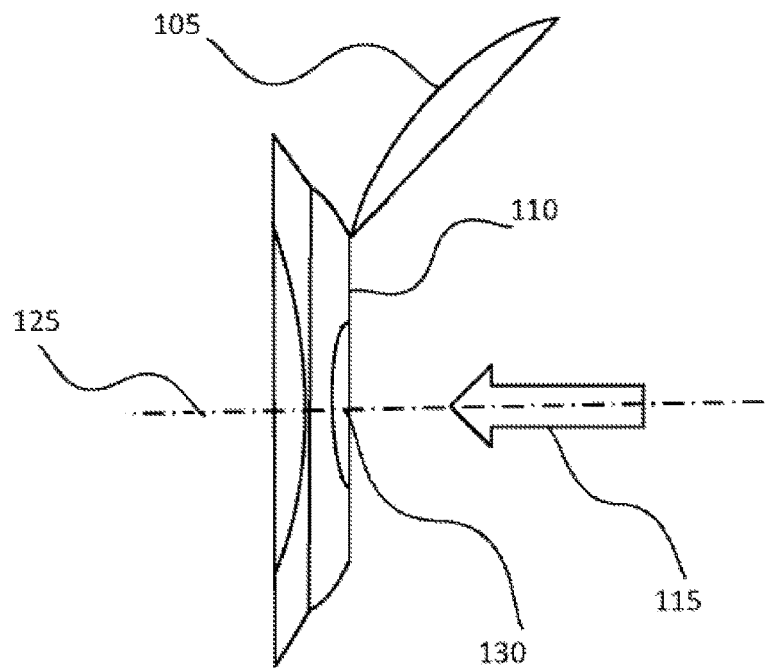
FIG. 1 shows a schematic side view of prior art cornea laser ablation after creating a flap.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

One or more embodiments of the invention are described below. It should be noted that these and any other embodiments described below are exemplary and are intended to be illustrative of the invention rather than limiting.

The preferred embodiments of the present invention will now be described with reference to the drawings. Identical elements in the various figures are identified with the same reference numerals.

Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a schematic side view of prior art cornea LASIK laser ablation after creating a flap. With the flap 105 lifted aside, a laser beam 115 may ablate the interior of the cornea 110 directly, removing material from an ablated area 130 by photo-ablation, a heat mediated process. In such surgery, the laser beam 115 may be directed substantially along the optical axis, a.k.a. the axis of vision 125.

The present invention improves on both the LASIK, and the prior Flapless LASIK method by, as an initial step, creating bubbles under the surface of the cornea in order to increase the speed of the laser beam penetrating into the area of corneal ablation. This improved Flapless LASIK procedure is a three-step procedure.

Figure 2:
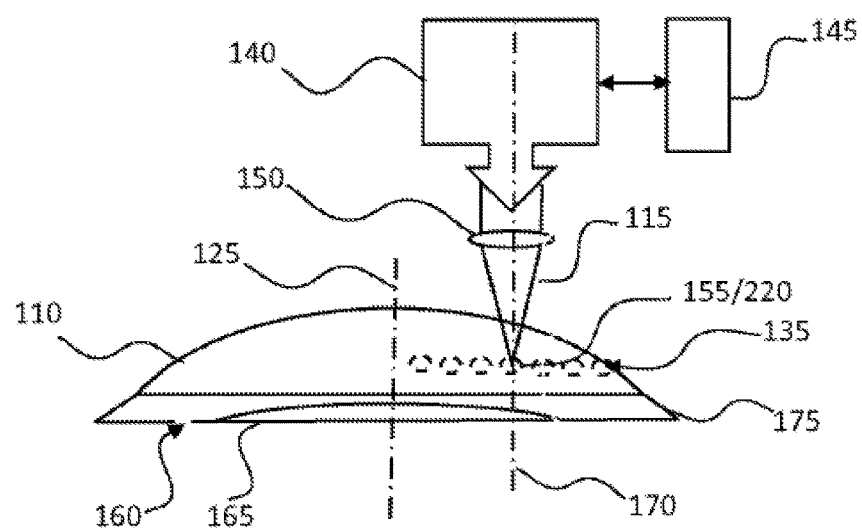
FIG. 2 shows a schematic side view of creating a row of bubbles by laser induced photo-disruption, a step in a process for removing material from an interior portion of a cornea of the present invention.

In the first step, shown in FIG. 2, a laser beam oriented near parallel, or at a greater angle, to the axis of vision creates one or more long and narrow rows of bubbles in the cornea of the eye. Such a bubble row or rows may lead to the regions that are to be ablated in subsequent steps.

Figure 5:
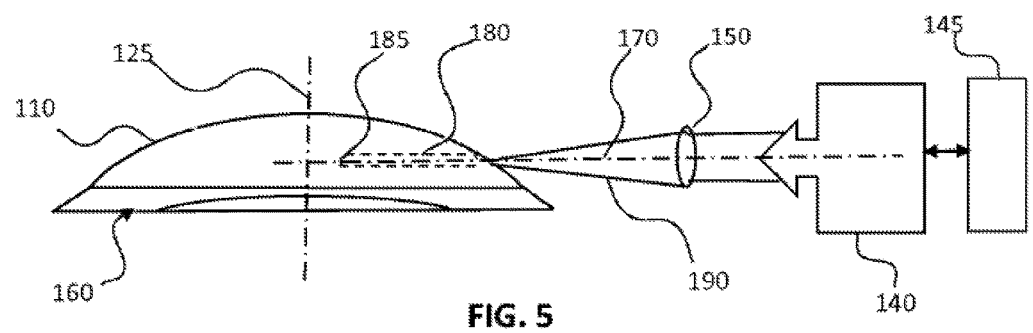
FIG. 5 shows a schematic side view of converting a row of bubbles into a micro-channel by laser induced ablation or multi-photon ablation, another step in a process for removing material from an interior portion of a cornea of the present invention.

In the second step, shown in FIG. 5, a femtosecond laser beam, directed through such bubble rows, reaches the stroma, between the inner (endothelial) and outer (superficial) cornea, creating a channel that is about perpendicular to the axis of vision or at a lesser or greater angle.

Figure 6:
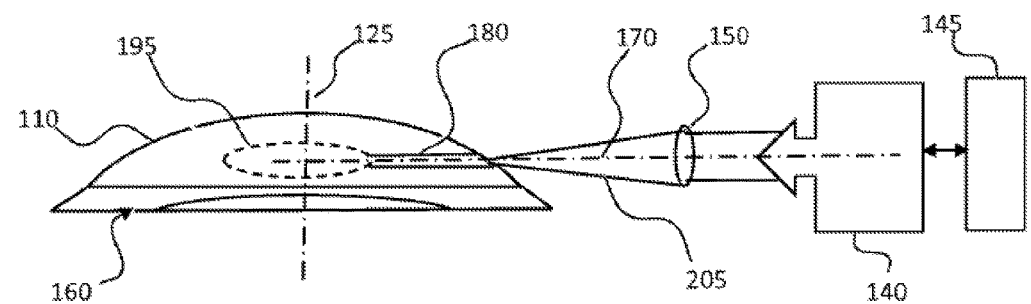
FIG. 6 shows a schematic side view of creating a void within an interior portion of a cornea by removing material using laser induced multi-photon ablation enabled by a laser directed down the temporary micro-channel, yet another step in a process for removing material from an interior portion of a cornea of the present invention.

In the third step, shown in FIG. 6, a femtosecond laser beam, after reaching the stroma, ablates the stroma at targeted spots.

While the present invention is directed toward creating a channel within the cornea to reach the stroma, it can be applied to other areas of the eye.

The steps of bubble creation, channel creation, and ablation of material can be accomplished by using one, two or three laser beams, whereby one or more laser sources may be used to generate the laser beams. For instance, a single laser source can be used that generates a single laser beam, preferably a femtosecond laser beam, that is divided into two beams, where the first beam performs the bubble creation and the second beam creates the channel and then ablates the target material. A second alternative would utilize two separate laser sources, where the first source generates the laser beam that creates the bubbles and the second source generates the laser beam that creates the channel and then ablates the target material. A third alternative would utilize a single laser source that emits a single laser beam at any given time and without splitting the beam, whereby the beam would initially be directed to create the bubbles, and once the bubbles were complete, the beam would be directed to create the channel and then ablate the material. A fourth alternative would utilize three separate laser beams, that would emit from one, two or three laser sources, whereby the first laser beam creates the bubbles, the second laser beam creates the channel, and the third laser beam ablates the target material.

The preferred laser beams consist of pulses in the range of 30 to 200 fsec duration, which could be longer or shorter, at repetition rates of 100 to 10,000 Hz, which could be higher or lower, and with varying intensities depending on the process or step being undertaken.

The First Step

In this initial step, shown in FIG. 2, a laser beam 115 of very low pulse energy, preferably in the range of 1 to 10 μA, though it may, with diminishing efficacy, be higher or lower, and with a focused intensity that is preferably in the range of $10^8$-$10^9$ W/cm$^2$, may be used. Any other such parameters that are sufficient to initiate a photo-disruption process may also be used, but may have significantly diminished efficacy. In one embodiment, a plurality of ultra-short laser pulses 115 are delivered to the eye approximately along, or parallel to, the vision axis 170, hence approximately perpendicular to the second laser beam used in the later steps shown in FIGS. 4 and 5. The laser may also be directed at different angles to the vision axis, though other angles tend to require more complex optical arrangements to achieve consistently good results. These pulsed may be used to create at least one row of bubbles 155 at depths of 150-250 μm below the surface of the cornea, although it could be shallower or deeper, that creates a string or row of bubbles, which may be created in an approximately straight line. A femtosecond or picosecond laser could be used to create the bubbles. This line of bubbles 155 is a precursor for the channel that is created in the second step.

FIG. 2 shows a schematic side view of this step of creating a row of bubbles 155 by laser induced photo-disruption. As seen in FIG. 2, a laser amplifier and power supply 140 may be interfaced to programmable control circuitry 145, and may be used to generate a pulsed laser beam 115 that may be focused down to produce a pulse intensity in a range of $10^8$ to $10^9$ W/cm$^2$ within a vicinity of the focal point. The laser beam 115 may, for instance, be focused by optical elements 150 such as, but not limited to, concave and convex spherical lenses, cylindrical lenses, prisms, beam-splitters, adjustable diaphragms, minors or some combination thereof. A bubble formed by photo-disruption 155 may be similar in diameter to the focus diameter 220 of the laser pulse, i.e., in a range from 10 μm to 100 μm. While creating the row of bubbles 135, the laser beam 115 may be directed substantially parallel to the optical axis, a.k.a. the axis of vision 125, thought the row of bubbles 135 may lie substantially perpendicular to this axis. This may be achieved by, for instance, by translating the optical elements 150 perpendicular to the axis of vision 125 in small incremental steps by means of a micro-transducer such as, but not limited to, a piezo-electric drive, a stepper motor controlled micrometer thread, or some combination thereof, all of which may be manipulated via the control circuitry 145. The row of bubbles may also be created by related methods such as, but not limited to, tilting the optics, using one or more steering mirrors, or some combination thereof.

The bubbles are created using photo-disruption and their creation does not damage the cornea, and in particular does not damage the thin area of cornea corresponding to the flap area of regular LASIK. The bubbles are created in the range of between tens of nanoseconds [1 nanosecond (1 nsec) $=10^{-9}$ sec] and tens of microseconds [1 microsecond (1 μsec)$=10^{-6}$ sec] before the main ablation channel is created, although that time span could be shorter or longer. Bubbles are typically created in one to two rows, but there can be more rows, next to each other on a plane approximately parallel to the surface of the cornea. The focused laser beam spot may be moved along the stroma, at a speed of approximately 0.25 mm/s or faster, to form a bubble region.

Figure 3:
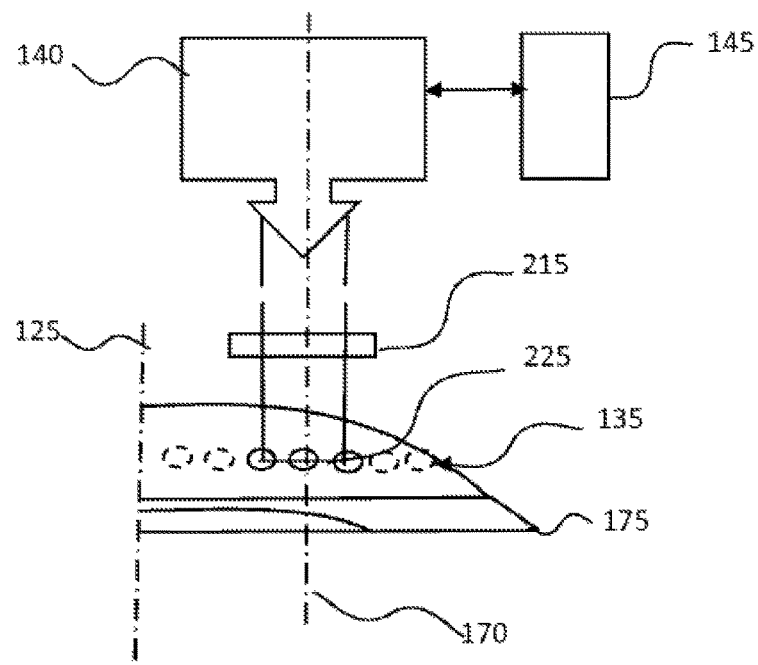
FIG. 3 shows a schematic side view of creating a row of bubbles by laser induced photo-disruption using a cylindrical lens.

In another embodiment of creating the bubble row or rows, shown in FIG. 3, a cylindrical lens 215 can be implemented with the laser 140 oriented approximately parallel to the axis of vision 125, which creates one row of bubbles 135 per single pulse from the laser. Thus one or more rows of bubbles can be created, stretching from the edge of the eye's cornea to the point of ablation in the stroma, in a shorter period of time than without the use of a cylindrical lens.

FIG. 3 shows a schematic side view of creating a row of bubbles by laser induced photo-disruption using a cylindrical lens 215. The laser amplifier and power supply 140 overseen by control circuitry 145 may generate a suitably shaped and powered beam that may be focused by the cylindrical lens 215 to form a focal line 225. The focal line may create the row of bubbles 135 in a single step, or may be stepped perpendicular to the axis of vision 125, creating the row of bubbles 135 in two or more steps. Using a focal line may increase the speed of the row creating process, but may require a higher powered laser to produce the required focused intensity to produce photo-disruption.

In another embodiment, a laser beam oriented approximately perpendicular to the axis of sight can sequentially create bubbles at varying depths, thereby creating a bubble row or rows.

In the event that the creation of the bubble row 135 or rows requires a shorter channel length without losing laser beam energy, an additional spherical lens can be applied. Such lens, with a diameter that can be approximately equal to the length of the cylindrical lens, is placed just above or below the cylindrical lens. The combination of these lenses both placed in the path of the laser beam can change the elongation of the laser beam to better match a distance from the entrance of the ablation laser beam into the cornea up to the desired area of stromal ablation.

Figure 4:
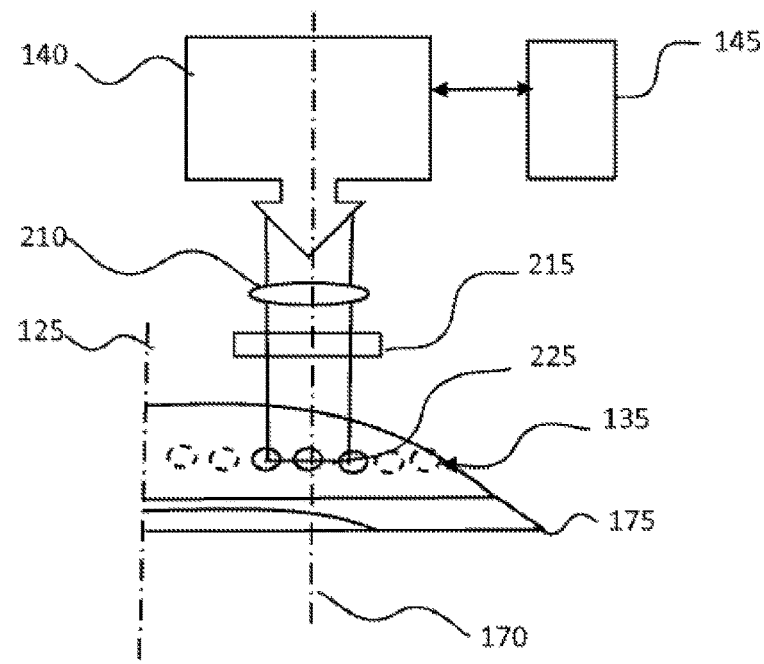
FIG. 4 shows a schematic side view of creating a row of bubbles by laser induced photo-disruption using a combination of a spherical lens and a cylindrical lens.

FIG. 4 shows a schematic side view of creating a row of bubbles by laser induced photo-disruption using a combination of one or more spherical lenses 210 and a cylindrical lens 215. The spherical lenses 210 may, for instance, act as beam shaping elements that may optimize the beam shape so that the spherical lens 210 may create a focal line 225 optimized for creating the row of bubbles 135 by photo-disruption.

In another embodiment, more than one bubble row may be created approximately parallel to one another in order to create a wider diameter channel. This may provide improved control of the channel's perpendicular size as well as a channel with improved uniformity, compared to a channel of the same diameter that is created using a single row of bubbles. The resulting channel may be ellipsoidal in shape with a width in the range of 50 to 100 μm, which may be smaller or greater.

While the focus size of a cylindrical lens $d_{cyl}$ without the use of a spherical lens may be in the range of 10 to 100 μm and elongated along the cylindrical lens axis, for example $\zeta_{cyl}=5$ mm, using a cylindrical lens in conjunction with a spherical lens of long focal length, hence large focal spot diameter, for example d=2 mm, will produce a focal spot length $\zeta_{cyl-d}=2$ mm practically without significant change of $d_{cyl-d} \approx d_{cyl}$.

The Second Step

In the second step, as shown in FIG. 5, a laser beam 190 creates the channel 180 by means of multi-photon ablation through the row or rows of bubbles by connecting by multi-photon ablation said row or rows of bubbles, where the channel typically extends from an outer (superficial) surface of the cornea 110 to a channel end point 185 located within said cornea (the endothelial cornea). The channel allows for ablation or removal of material at the channel end point as well as along the channel.

This channel creating laser beam has a preferred pulse energy range of 0.1 mJ to 1 mJ and a focus diameter range of 10 μm to 100 μm, although each of these variables could be less than or greater than specified herein. The channel is created using multi-photon ablation, which requires a pulse intensity of $10^{12}$ watts/cm$^2$ or greater, although a pulse intensity in the range of $10^{13}$-$10^{15}$ W/cm$^2$ is preferred. As the pulse intensity increases, the probability of initiating multi-photon ablation on a given pulse increases. However, higher energies will create wider channels, which may be less desirable. Use of lower pulse intensity that creates the channel via photo-ablation is possible, but this would result in thermal damage that would cause a longer channel closure and a longer healing time.

The Third Step

Once the channel is created, the energy level of the laser beam may be kept constant or it may be increased, preferably by a factor of from 2 to 5 in comparison to the laser pulse energy for creation of the channel, or a different laser beam may be used at such energy levels. The pulse intensity is preferably increased to or maintained in the range of $10^{13}$-$10^{15}$ W/cm$^2$, and by focusing the laser at targeted tissue, the tissue is removed by multi-photon ablation. Keeping the energy of each laser pulse at approximately a constant value for the given pulse duration and the focal spot size is important to reach and maintain the approximately constant intensity for multi-photon ablation of live tissue. The channel may, for instance, also provide a means of removal of the ablated material in the form of a gas or a liquid, or a combination thereof. The removal of the ablated material may, for instance, occur as the result of a pressure differential between the void and the ambient room pressure. The procedure may, for instance, be conducted in a reduced pressure environment to provide improved removal of the ablated material. A separate channel or channels may alternatively be provided for the removal of the ablated material.

FIG. 6 shows a schematic side view of this step of creating a void 195 within an interior portion of the cornea 110 by removing material using laser induced multi-photon ablation enabled by laser beam consisting of a second plurality of ultra-short laser pulses 205 directed down the temporary micro-channel 180. The laser amplifier and power supply 140, under control of programmable circuitry 145, may, for instance, produces pulses having energies in a range of 0.1 mJ to 5 mJ. These pulses may be focused down by optical elements 150 to produce pulse intensities in a range of $10^{12}$ to $10^{15}$ W/cm$^2$. These high intensity pulses may induce multi-photon ablation within the temporary micro-channel 180 or in a vicinity of the micro-channel end point 185.

By changing the position of the focusing lens or focusing minor, the location of the ablation spot can be moved along the channel. Controlling the number of laser pulses for each spot controls the amount of ablated material in each spot. By increasing the number of laser pulses more material will be ablated per unit of time, and by decreasing the number of laser pulses less material will be ablated per unit of time.

By maintaining the pulse repetition rate, preferably in the range of 1 kHz or greater during this third step, the channel opening can be controlled or maintained until the desired ablations and procedures can be completed. Once the procedures are complete, the channel will spontaneously close and heal within several minutes, most of the time in less than 3 minutes, whereby smaller diameter channels may heal faster than larger diameter channels.

Multi-Photon Ablation

The second and third steps are preferably accomplished using "multi-photon ablation". Multi-photon ablation is a completely different method of material removal than photo-ablation. Multi-photon ablation requires a high laser pulse intensity, equal to or higher than $10^{12}$ W/cm$^2$ and preferably in the range of $10^{13}$-$10^{15}$ W/cm$^2$, in order to remove particles, i.e. molecules and atoms, from targets. Multi-photon ablation operates by means of instantaneous absorption of several photons, faster than the molecule's or atom's relaxation time, and creates an ultra-high electric field in the vicinity of such particles. This causes a non-thermal ablation of matter, whereas other laser based ablation methods are thermal.

For example, a 5 mJ pulse with 50 femtosecond pulse duration focused down to a diameter of 10 to 100 µm provides a pulse intensity in the range of $10^{13}$-$10^{15}$ W/cm$^2$. At such intensities particles (molecules, atoms) at the surface of the target material, for instance tissue, are under a very high electric field, which may exceed the work force, or bounding, of a molecule or atom to the target such as tissue material, therefore freeing them from the target surface and creating the effect of ablation but practically without heating the target material.

Initiating multi-photon ablation with a given laser pulse is based on probability that is most affected by the pulse intensity. So, while multi-photon ablation may be possible below an intensity of $10^{12}$ W/cm$^2$, the probability that a given pulse causes multi-photon ablation at lower intensities is significantly lower. As such, descriptions herein of multi-photon ablation processes do not preclude the possibility that certain laser pulses within such processes will fail to invoke multi-photon ablation and that certain pulses may thereby invoke photo-ablation.

Figure 7:
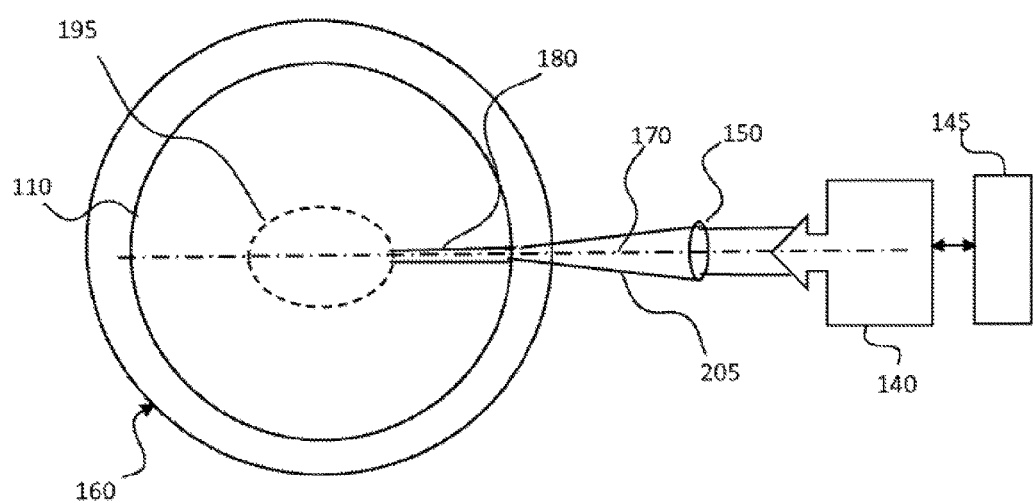
FIG. 7 shows a schematic plan view of creating a void within an interior portion of a cornea by removing material using laser induced multi-photon ablation enabled by a laser directed down the temporary micro-channel.

FIG. 7 shows a schematic plan view of creating a void 195 within an interior portion of a cornea 110 by removing material using laser induced multi-photon ablation enabled by a laser 140 directed down the temporary micro-channel 180.

Benefits of Bubble Creation

The second and third steps can alternatively be performed as described without initially performing the first step of bubble creation. However, creating the bubbles prior to creating the channel provides several benefits in addition to those benefits provided in creating the channel without first creating the bubbles. First, implementing the bubble creation step increases the speed of the ablation channel's creation in the cornea. For example, the speed of creation of a 3 mm channel from the edge of the cornea to the area required for ablation was 1.5-2 times faster than without bubbles, all other conditions being the same. Second, the bubble creation provides for a more uniform channel diameter, which significantly increases the uniformity of the laser beam from shot-to-shot while traveling to the spot of ablation, improving the precision of the ablation. As seen from comparing the ablation times between ablation of material where the channel was created with and without the initial bubble creation step, this increased channel uniformity decreases losses of energy of the laser pulses, which allows for the effective and practical use of a lower level of pulse intensity for the multi-photon ablation of target materials by as much as about an order of magnitude.

Other Applications

While the procedures disclosed herein are described as they apply to the eye, they may alternatively be applied to create channels in material or organic tissue, for example whereby the bubbles are initially created in the organic tissue using photo-disruption, fsec laser pulses then create the channel through the bubbles using multi-photon ablation, and if ablation is desired fsec laser pulses ablate matter using multi-photon ablation or other ablation techniques.

Additionally, once a channel is created via steps 1 and 2, or via step 2, described herein, procedures other than ablation may be implemented through the channel, or material, drugs, or devices may be inserted through the channel.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method of removing material from an internal portion of an eye comprising:
   creating a first row of bubbles below the surface of the eye with a first laser beam, wherein all of said bubbles in said first row of bubbles are linearly aligned;
   creating a channel through the linearly aligned first row of bubbles with a second laser beam; and
   multi-photon ablating material located along or at the end of said channel with said second laser beam.

2. The method of claim 1 wherein said channel is created from $10^{-9}$ seconds to $10^{-6}$ seconds after said first row of bubbles is created.

3. The method of claim 2 wherein said first laser beam creating said first row of bubbles has a pulse intensity of from $10^8$ to $10^9$ W/cm$^2$; said second laser beam creating said channel through said first row of bubbles has a pulse intensity of from $10^{11}$ to $10^{15}$ W/cm$^2$; and said second laser beam ablating the material has a pulse intensity from $10^{12}$ to $10^{15}$ W/cm$^2$.

4. The method of claim 3 wherein said first laser beam creating said first row of bubbles has a pulse energy of from 1 to 10 µJ; said second laser beam creating said channel through said first row of bubbles has a pulse energy of from 0.1 mJ to 1 mJ; and said second laser beam ablating the material has an energy level from 0.1 mJ to 5 mJ.

5. The method of claim 4 wherein said second laser beam creating said channel through said first row of bubbles has a focus diameter from 10 µm to 100 µm.

6. The method of claim 4 wherein said multi-photon ablation of material is conducted with pulses having a repetition rate of 1 KHz or greater.

7. The method of claim 4 wherein pulses of said first laser beam that creates a first row of bubbles below the surface of the eye are delivered along the axis of vision; and wherein said first row of bubbles are created perpendicular to the axis of vision.

8. The method of claim 4 wherein said first row of bubbles are created at a depth from 150 μm to 250 μm below the surface of the eye's cornea.

9. The method of claim 4 wherein the pulses of said second laser beam has a duration from 30 to 200 fsec.

10. The method of claim 4 wherein the pulses of said second laser beam has a repetition rate from 100 to 10,000 Hz.

11. The method of claim 4 wherein a single initial laser beam is divided to create said first laser beam that creates said first row of bubbles and said second laser beam that creates said channel and ablates said material.

12. The method of claim 4 wherein more than one row of bubbles are created, and said creation of the channel is through more than one row of bubbles.

13. The method of claim 2 wherein said channel extends from an outer surface of the eye's cornea to an end point within the eye's cornea.

14. The method of claim 2 wherein said material that is ablated consists of at least a portion of the eye's stroma.

15. The method of claim 14 wherein said ablation of the stroma improves the refractive properties of the eye's cornea.

16. The method of claim 2: wherein the row of bubbles is created below the surface of the eye's cornea; wherein creating the channel through the row of bubbles with said second laser beam comprises creating a temporary micro-channel extending from a surface of said cornea to a micro-channel end point located within said cornea by delivering a first plurality of ultra-short laser pulses through said row of bubbles; and wherein ablating said material located along or at the end of said channel with said second laser beam comprises delivering a second plurality of ultra-short laser pulses with pulse energies of 20 μJ or greater and focused down to a pulse intensity in a range of $10^{12}$ to $10^{15}$ W/cm$^2$ and thereby generating a void.

* * * * *